(12) United States Patent
Attia

(10) Patent No.: US 8,579,976 B2
(45) Date of Patent: Nov. 12, 2013

(54) EXPANDABLE CAGE FOR VERTEBRAL SURGERY INVOLVING LUMBAR INTERSOMATIC FUSION BY A TRANSFORAMINAL POSTERIOR APPROACH

(75) Inventor: David Attia, Montelimar (FR)

(73) Assignees: David Attia (FR), part interest; Gerald Schaumburg (FR), part interest; Francisco Ros Guillen (FR), part interest ( * ) Notice: Subject to any disclaimer, the term of this patent is extended or adjusted under 35 U.S.C. 154(b) by 132 days.

(21) Appl. No.: 12/664,379

(22) PCT Filed: Jun. 12, 2007

(86) PCT No.: PCT/FR2007/051425
§ 371 (c)(1),
(2), (4) Date: Jun. 8, 2010

(87) PCT Pub. No.: WO2008/155472
PCT Pub. Date: Dec. 24, 2008

(65) Prior Publication Data
US 2010/0262246 A1    Oct. 14, 2010

(51) Int. Cl.
*A61F 2/44* (2006.01)
(52) U.S. Cl.
USPC ..................................... 623/17.11

(58) Field of Classification Search
USPC .......................................... 623/17.11–17.16
See application file for complete search history.

(56) References Cited

U.S. PATENT DOCUMENTS

| 7,655,046 B2 * | 2/2010 | Dryer et al. ................. 623/17.15 |
| 2004/0127994 A1 * | 7/2004 | Kast et al. .................. 623/17.16 |
| 2006/0129244 A1 | 6/2006 | Ensign |
| 2006/0287725 A1 | 12/2006 | Miller |

FOREIGN PATENT DOCUMENTS

| EP | 1 415 622 A1 | 5/2004 |
| FR | 2861582 A1 | 5/2005 |

* cited by examiner

*Primary Examiner* — Mary Hoffman
(74) *Attorney, Agent, or Firm* — Blank Rome LLP

(57) ABSTRACT

An implant of the intersomatic cage type, for fusion of vertebral bodies by a transforaminal approach, is disclosed that comprises a body with a curved profile that is designed to be implanted between the vertebral plates of two adjacent vertebrae. According to the invention, said body of curved profile comprises a posterior maneuvering part and an anterior attack part, said anterior attack part being composed of a lower tongue and of an upper tongue that are designed to receive between them a spacer element that can slide between a position of introduction, in which it is situated near said posterior maneuvering part, and a spacing position, in which it is situated near the end of said anterior attack part, thus increasing the thickness of the latter by spreading the tongues apart, said spacer element comprising a receiving seat that is open at the top and bottom.

5 Claims, 1 Drawing Sheet

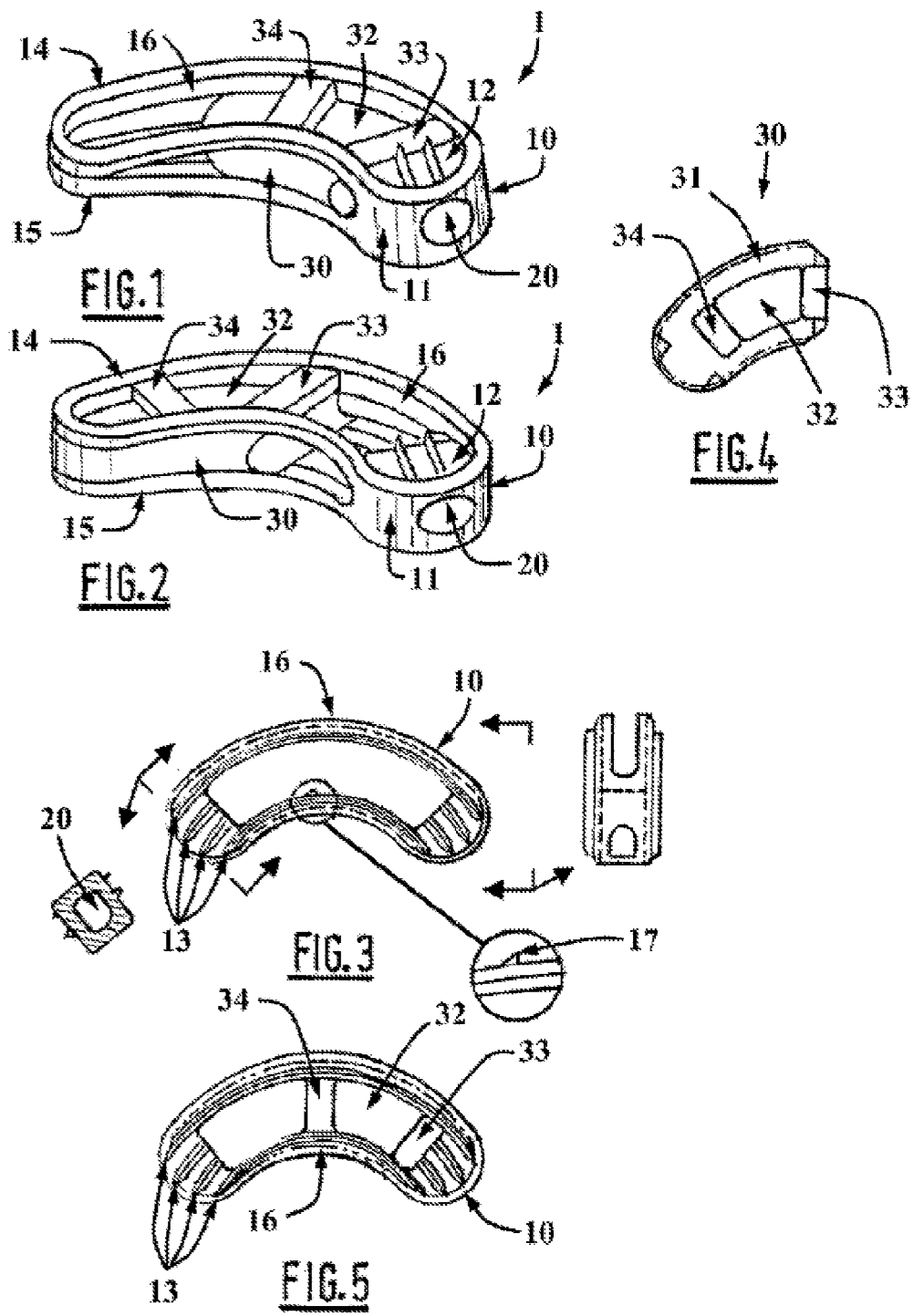

EXPANDABLE CAGE FOR VERTEBRAL SURGERY INVOLVING LUMBAR INTERSOMATIC FUSION BY A TRANSFORAMINAL POSTERIOR APPROACH

CROSS-REFERENCE TO RELATED APPLICATIONS

This application is a National Phase Application of PCT/FR2007/051424, filed on Jun. 12, 2007, the contents of which are hereby incorporated by reference.

FIELD OF INVENTION

This invention relates to an implant, called a cage, that is used in vertebral surgery for the fusion of two vertebral bodies of a vertebral column and is inserted between the vertebral bodies using a posterior transforaminal approach. That operation is known as a TLIF (transforaminal lumbar interbody fusion).

BACKGROUND OF THE INVENTION

A conventional cage implant is described, for example, in patent application FR2861582. Its external profile is curved in a bean-shaped and is designed to be inserted between two vertebrae using the posterior transforaminal approach. In other words, the axis of the implant, according to which it is inserted into the disc space, is curved. The implant has an interior cavity designed to contain either a natural or synthetic bone graft material, which is why the implant is referred to as a "cage." The cage is open at both the upper and lower ends to allow the bone graft to come into contact with the respective vertebral bodies in order to achieve a definitive fusion between the vertebral bodies.

Intersomatic arthrodesis is performed using a posterolateral approach following resection of all or part of the posterior facet joints, through an interstice between the dural sheath and underlying root. Once inserted, the implant moves to the anterior part of the disc space by rotating 90° between the vertebral bodies to reach its final position, expanding transversally in the disc space.

The implant is pre-filled with a bone graft material prior to insertion. That is because, once placed in its final position, the implant is no longer accessible.

The insertion of that type of implant into often highly-pinched discs requires placement of pedicular screws beforehand to open up the disc space. Furthermore, another complicating factor is the difficulty of turning the implant 90° in such a restricted space while rotating it at the same time because the screws only open the posterior part of the disc space.

Expandable implants have been proposed to allow for more effective opening of the disc space than with a pedicular screw. For example, U.S. Patent Application Serial No. 2006/0129244 describes an expanding device designed to be inserted between two vertebral bodies that is composed of two plates and an expanding part that slides between the two plates along the axis of the implant in order to separate the two plates between an unexpanded position and an expanded position.

That type of device will provide for better opening of the disc space. However, it is still very difficult or even impossible to insert bone graft material using such a device, particularly into the anterior part of the implant.

Accordingly, it is an object of this invention to provide an implant that can be inserted using an anterior transforaminal approach between two adjacent vertebrae, and allows for easy insertion of bone graft material.

SUMMARY OF THE INVENTION

To solve at least the problems and/or disadvantages described above, and to provide at least the advantages described below, a non-limiting object of the present invention is to provide a surgical implant of the intersomatic cage type for the fusion of vertebral bodies using a transforaminal approach, comprising a curved profile designed to be implanted between the vertebral plates of two adjacent vertebrae and at least one inner space opened above and below configured to contain a bone graft material. The body of the curved profile comprises a posterior manipulation part and an anterior leading part, with the anterior leading part being composed of a lower tongue and an upper tongue that are designed to receive between them an expanding element that can slide between an insertion position, in which it is situated near the posterior manipulation part, and an expanded position, in which it is situated near the end of the anterior leading part, thus increasing the thickness of the latter by spreading the tongues apart, and the expanding element comprising a receiving exposed section at the top and bottom and designed to receive the aforementioned bone graft material in the insertion position and to bring it into the anterior part of the vertebral plates in the expanded position.

The leading end designates the end designed to be inserted between the vertebral bodies and the manipulation end designates the opposite end on which the force is exerted to push the device between the vertebral plates.

Sliding the expanding element also expands the cage and brings the bone graft material into the anterior zones of the intervertebral space that are difficult to reach.

The expanding element is advantageously comprised of two transverse partitions that separate the exposed section designed to receive the bone graft material. The height of the partitions is equal to that of the implant in its expanded position and their width is equal to that of a central opening formed by each of the tongues.

As such, the expanding element forms a sliding core between the tongues separated by the partitions, the height of which is always the same and can thus transport the graft to the anterior part of the implant.

At least one of the tongues is advantageously equipped with mechanisms to securely lock the expanding element in the expanded position.

The curved profile is advantageously shaped like a bean.

The external surfaces of the tongues are advantageously equipped with ribs designed to grip the plates of the vertebral bodies.

The manipulation end is advantageously equipped with an opening through which the expanding element can be manipulated and a secondary bone graft material can be inserted once the expanding element is in the expanded position.

BRIEF DESCRIPTION OF THE FIGURES

This invention can be better understood by reading the following description of a non-restrictive realisation example, in reference to the appended illustrations where:

FIG. 1 is a perspective view illustrating an implant according to this invention in the insertion position;

FIG. 2 is a perspective view illustrating the implant shown in FIG. 1 in the expanded position;

FIG. 3 is a plan view from below illustrating a principal profile of the device shown in FIGS. 1 and 2;

FIG. 4 is a plan view from below illustrating an expansion element of the device shown in FIGS. 1 and 2; and FIG. 5 is a plan view from below illustrating the device shown in FIG. 2.

DETAILED DESCRIPTION OF THE EXEMPLARY EMBODIMENTS

Reference will now be made in detail to non-limiting embodiments of the present invention by way of reference to the accompanying drawings, wherein like reference numerals refer to like parts, components and structures.

With reference to FIGS. 1 to 5, the surgical implant 1 is of the intersomatic cage type for the fusion of vertebral bodies using a transforaminal approach. The implant 1 is made of a biocompatible elastic material. The implant is advantageously made of an implantable-grade polyetheretherketone (PEEK) polymer. Alternatively, it may be made of a metal such as titanium or a bioresorbable material such as a poly-L-lactic (PLLA) material.

In general, the implant 1 is comprised of a body 10 in the form of a bean designed to be implanted between the plates of two adjacent vertebrae, one expanding element 30 forming a core therein designed to be filled with bone graft material that slides inside of the body 10. The expanding element 30 is designed to slide along the body's 10 curved axis between an implant in insertion position in which the expanding element 30 is located in a posterior position of the body 10, as, shown in FIG. 1, and an expanded position in which the expanding element 30 is located in an anterior position of the body 10, as shown in FIG. 2.

The body 10 forms a single block made by injection molding or machining comprised of a posterior manipulation part 11 and an anterior leading part. The posterior manipulation part 11 is generally in the form of a half-ring closed at the top and bottom by upper and lower partitions 12 equipped with ribs 13 on their external surfaces that extend along the axis of the body 10. Those ribs 13 are designed to grip the plates of the vertebrae. The posterior end of the ring-shaped part is equipped with an opening 20 through which the expansion element 30 can be manipulated and the posterior part of the cage can be filled with bone graft material after expansion of the expansion element 30.

The anterior leading part makes up the major part of the body 10 and is comprised of an upper tongue 14 and a lower tongue 15 that respectively extend from the upper and lower ends of the posterior manipulation part 11. The tongues 14 and 15, which are substantially identical in form, are hollow in the center such that they are comprised of lateral edges 16 that extend along the axis of the body 10 and a tip identical in form to that of the partition fitted at the opposite end in the posterior manipulation part 11. As in the case of the upper and lower partitions 12, ribs 13 have been formed on the outer surface of that tip. The ribs 13 on the tip and upper and lower partitions 12 that are located on the same axis as the lateral edges 16 are extended on the lateral edges to form two lateral ribs 13 that extend along the curved axis of the body 10 and are designed to grip the plate of the corresponding vertebral body.

Locking elements 17 are fitted under the lateral edges 16. The locking elements 17, one of which is called out in an enlarged view in FIG. 3, are provided with one gently sloping edge that is compressed by the expanding element 30 when it slides from the insertion position to the expanded position and a vertical edge that elastically straightens behind the expanding element 30 once released by the expanding element. The locking element 17 is positioned so as to be released when the end of the expanding element 30 is located at the anterior end of the tongues 14 and 15, thus locking the implant in the expanded position.

The lateral edges 16 have been equipped with guiding elements to work together with corresponding guiding elements on the expanding element 30 such that the expanding element 30 slides inside of the body 10 along its axis.

The expanding element 30 is comprised of two lateral edges 31 with the same curvature and same spacing as corresponding lateral edges 16 on the body 10. Those two edges 31 come together at an anterior end with a curved end, the form of which is designed to extend the tips of the tongues 14 and 15 of the body 10 in expanded position in order to reproduce a form similar to that of the posterior manipulation part 11 of the body 10. Furthermore, the height of the expanding element 30 added to the height of the tongues 14 and 15 corresponds exactly to the height of the posterior manipulation part 11. In that manner, when in expanded position, the height of the implant 1 is identical throughout its length and its profile is that of a generally symmetrical bean corresponding to that of previous types of implants.

The expanding element 30 is comprised of an open section 32 on the top and bottom thereof that is designed to receive a bone graft material. Two transversal partitions 33 and 34 have been created, one at the posterior end of the expanding element 30 and the other near its anterior end, slightly set back from a curved anterior part. The height of the partitions 33 and 34 is identical to that of the posterior manipulation part 11, meaning the height of the body 10 in expanded position. Furthermore, their width is that of the space between the lateral edges 16 of the tongues 14 and 15, meaning the width of the central opening formed in each of the tongues 14 and 15.

When in the insertion position shown in FIG. 1, in which the expanding element 30 is positioned against the posterior manipulation part 11 of the body 10, the implant is prefilled with bone graft material in a space formed between the partitions 33 and 34 and lateral partitions formed by the lateral edges 16 of the tongues 14 and 15 where they extend away from the expanding element 30. After insertion of the implant 1 between the vertebral bodies, the expanding element 30 is then pushed so that it slides between the tongues 14 and 15. That movement expands the space between the tongues 14 and 15. The front part of the expanding element 30 forces the tongues 14 and 15 to a height substantially equal to that of the partitions 33 and 34 as it slides along the axis of the body 10, such that the transplant is always located in the open section 32 formed by the partitions 33 and 34 and the lateral edges 16 so there is no risk of the bone graft material leaking.

In other words, the expanding element 30 forms an open section 32 that brings the bone graft material to the anterior end of the implant 1. Once the anterior end of the expansion element 30 reaches the anterior ends of the tongues 14 and 15, the locking mechanisms 17 are triggered and immobilize the implant 1 in the expanded position as shown in FIG. 2. The section separated by the partition 33 and the posterior manipulation part 11 of the implant 1 could then, if necessary, be filled with bone graft.

The foregoing description and drawings should be considered as illustrative only of the principles of the invention. The invention may be configured in a variety of shapes and sizes and is not intended to be limited by the preferred embodiment. Numerous applications of the invention will readily occur to those skilled in the art. Therefore, it is not desired to limit the invention to the specific examples disclosed or the exact construction and operation shown and described. Rather, all suitable modifications and equivalents may be resorted to, falling within the scope of the invention.

The invention claimed is:

1. A surgical implant for the fusion of vertebral bodies using a transforaminal approach, comprising:
a body with a curved profile designed to be implanted between vertebral plates of two adjacent vertebrae, wherein the body comprises:
(i) a posterior manipulation end comprising a half-ring, and
(ii) an anterior leading end having a lower tongue and an upper tongue that extend from upper and lower ends of the posterior manipulation end, such that the tongues are connected to each other at the posterior manipulation end by a connection portion integral with both the lower tongue and the upper tongue; and
an expanding element, disposed between the lower and upper tongues, configured to slide between an insertion position in which the expanding element is situated near the posterior manipulation end while tips of the tongues are next to each other, and an expanded position in which the expanding element is situated near the anterior leading end, thus increasing a distance between the tongues by forcing the tongues apart, the expanding element comprising an open section that is open at a top and bottom portion thereof and that is designed to receive bone graft material in the insertion position and to bring the bone graft material into an anterior part of the vertebral plates in the expanded position, the expanding element comprising two transversal partitions that define the open section configured to receive the bone graft material, the height of the partitions being equal to that of the implant in the expanded position and their width being that of a central opening in each of the tongues.

2. The surgical implant according to claim 1, wherein at least one of the tongues is equipped with mechanisms to securely lock the expanding element in the expanded position.

3. The surgical implant according to claim 1, wherein the body is in the form of a bean.

4. The surgical implant according to claim 1, wherein external surfaces of the tongues are equipped with ribs designed to grip the plates of the two adjacent vertebrae.

5. The surgical implant according to claim 1, wherein the posterior manipulation part is equipped with an opening through which the expanding element can be handled and a secondary amount of bone graft material can be inserted once the expanding element is in the expanded position.

* * * * *